United States Patent [19]

Belagaje et al.

[11] Patent Number: 4,752,577

[45] Date of Patent: Jun. 21, 1988

[54] METHOD FOR USING A NOVEL TRANSCRIPTIONAL- AND TRANSLATIONAL-ACTIVATING SEQUENCE IN STREPTOMYCES

[75] Inventors: Ramamoorthy Belagaje; Jeffrey T. Fayerman; Mark A. Richardson, all of Indianapolis, Ind.

[73] Assignee: Eli Lilly and Company, Indianapolis, Ind.

[21] Appl. No.: 650,158

[22] Filed: Sep. 13, 1984

[51] Int. Cl.$^4$ .................. C12N 15/00; C12N 5/00
[52] U.S. Cl. ........................... 435/68; 435/70; 435/169; 435/170; 435/172.1; 435/172.3; 435/183; 435/243; 435/253; 435/317.1; 435/820; 435/822; 435/886; 536/27; 935/23; 935/27; 935/41; 935/56; 935/75
[58] Field of Search ............ 435/70, 170, 169, 172.1, 435/172.3, 183, 243, 253, 317, 320, 820, 822, 886, 68; 536/27; 935/23, 27, 38–41, 44, 45, 46, 52, 56, 58, 66, 75

[56] References Cited

U.S. PATENT DOCUMENTS

| | | | |
|---|---|---|---|
| 4,332,898 | 6/9182 | Reusser | 435/172.3 |
| 4,332,900 | 6/1982 | Manis | 435/172.3 |
| 4,362,816 | 12/1982 | Reusser | 435/172.3 |
| 4,362,817 | 12/1982 | Reusser | 435/172.3 |
| 4,416,994 | 11/1983 | Nakatsukasa | 435/253 |
| 4,460,689 | 7/1984 | Foor | 435/172.3 |
| 4,468,462 | 8/1984 | Malin | 435/253 |
| 4,495,280 | 1/1985 | Bujard | 435/6 |
| 4,503,155 | 3/1985 | Miller | 435/172.3 |
| 4,508,826 | 4/1985 | Foor | 435/235 |
| 4,513,085 | 4/1985 | Nakatsukasa | 435/253 |
| 4,513,086 | 4/1985 | Fayerman | 435/317 |
| 4,599,300 | 12/1985 | Kovacevic | 435/68 |
| 4,599,302 | 12/1985 | Ingolia | 435/172.3 |

OTHER PUBLICATIONS

*Microbiology,* Third Edition, B. D. Davis et al., Harper & Row, Pub., Philadelphia. (1980), pp. 744–750.
Jones, M. D. et al., Plasmid, 11(1): 92–95 (1984), "pFJ265, A New Cloning Vehicle for Streptomyces".
BRL Catalogue & Reference Guide (1983), pp. 72–75.
Moran et al., 1982, Molecular General Genetics, 186:339.
Bibb and Cohen, 1982, Molecular General Genetics, 187:265.
Meyer et al., 1983, Gene, 23:25.
Jaurin and Cohen, 1984, Gene, 28:83.

*Primary Examiner*—Margaret Moskowitz
*Attorney, Agent, or Firm*—Gerald V. Dahling; Leroy Whitaker

[57] ABSTRACT

The present invention is a method for expressing functional polypeptides in Streptomyces using a recombinant DNA expression vector comprising a novel transcriptional- and translational- activating sequence. The novel activating sequence can be synthesized by conventional methods and used in Streptomyces expression vectors. One such vector, plasmid pFJ350, expresses and confers hygromycin resistance in Streptomyces host cells.

28 Claims, 1 Drawing Sheet

Restriction Site and Function Map of Plasmid pFJ350
(8 kb)

METHOD FOR USING A NOVEL TRANSCRIPTIONAL- AND TRANSLATIONAL-ACTIVATING SEQUENCE IN STREPTOMYCES

The present invention comprises a method for using a novel transcriptional- and translational-activating DNA sequence for expression of a functional polypeptide in Streptomyces. The invention further comprises the vectors, transformants and novel transcriptional-and translational-activating sequence required to employ the aforementioned method.

The present invention provides a method for expressing functional polypeptides in Streptomyces host cells by means of recombinant DNA technology. Heretofore, the development and exploitation of recombinant DNA technology in Streptomyces have been retarded and made especially difficult because of the general lack of suitable cloning and expression vectors. This paucity of expression vectors is explained in part by the frequent lack of recognition afforded foreign transcriptional- and translational-activating signals in Steptomyces. Consequently, the well known trp (Hallewell, R. A. and S. Emtage, 1980, Gene 9:27), lac (Guarante, L. et al., 1980, Cell 20:543 and Roberts, T. M. et al., 1979, Proc. Nat. Acad. Sci USA 76:5596), and lpp (Lee, N. et al., 1981, J. of Bacteriol. 146:861; Zwiebel, L. J. et al., 1981, J. of Bacteriol. 145:654 and Nakamura, K. and M. Inouye, 1979, Cell 18:1109) transcription- and translation-directing promoter systems are not known to be functional in Streptomyces. Thus, few foreign and practically no eukaryotic genes have been expressed in the Streptomyces host system.

The extremely limited ability of Streptomyces to recognize foreign transcription and translation signals necessitates the development of alternate signals that are recognized. Accordingly, a novel transcriptional- and translational-activating sequence was synthesized to direct the expression of virtually any polypeptide in Streptomyces. This method for expressing polypeptides in Streptomyces represents a significant advance in the technical art and greatly expands the application of recombinant DNA technology in Gram-positive microorganisms.

Gene cloning and expression of products in Streptomyces are highly advantageous since the organism is substantially non-pathogenic and ordinarily does not produce endotoxins. In addition, the life-cycle of Streptomyces has been extensively studied and is well known and understood in the antibiotic and fermentation industries. The present method, associated expression vectors and transformants are particularly important because they allow for the commercial exploitation of these important advantages.

For purposes of the present invention, as disclosed and claimed herein, the following terms are as defined below.

Recombinant DNA Expression Vector—any autonomously replicating or integrating agent, including, but not limited to, plasmids, comprising a DNA molecule to which one or more additional DNA segments can be or have been added and expressed.

Transformation—the introduction of DNA into a recipient host cell that changes the genotype and consequently results in a change in the recipient cell.

Transformant—a recipient host cell that has undergone transformation.

Restriction Fragment—any linear DNA generated by the action of one or more restriction enzymes.

Functional Polypeptide—a recoverable bioactive entirely heterologous or homologous polypeptide or precursor, a recoverable bioactive polypeptide comprising a heterologous polypeptide and a portion or whole of a homologous polypeptide or a recoverable bioinactive fusion polypeptide comprising a heterologous polypeptide and a bioinactivating homologous polypeptide which can be specifically cleaved.

Fused Gene Product—a recoverable heterologous polypeptide which is fused with a portion or whole of a homologous polypeptide.

Insertional Isomer—one of the two or more possible recombinant DNA molecules formed when a DNA fragment is inserted at one of two or more compatible sites on the recipient DNA.

$Thio^R$—the thiostrepton-resistant phenotype or gene conferring same.

$Amp^R$—the ampicillin-resistant phenotype or gene conferring same.

$Tet^S$—the tetracycline-sensitive phenotype.

$Neo^R$—the neomycin-resistant phenotype or gene conferring same.

$Hm^R$—the hygromycin-resistant phenotype or gene conferring same.

DETAILED DESCRIPTION OF THE INVENTION

The present invention is a method for expressing a functional polypeptide in Streptomyces which comprises:
(1) transforming a restrictionless Streptomyces host cell with a selectable recombinant DNA expression vector capable of autonomous replication or integration in said host cell, said vector comprising:
(a) the transcriptional- and translational-activating sequence

```
5' TTTGACAAAAATGGGCTCGTGTTGTATAATA
   |||||||||||||||||||||||||||||||
3' AAACTGTTTTTACCCGAGCACAACATATTAT

AATGTAAGCTTGTGAGGTGGATGCCATG 3'
   ||||||||||||||||||||||||||||
   TTACATTCGAACACTCCACCTACGGTAC 5'
``` wherein
A is deoxyadenyl,
G is deoxyguanyl,
C is deoxycytosyl and
T is thymidyl,
and
(b) a DNA sequence that codes for a functional polypeptide positioned for expression and in the translational reading frame of said transcriptional- and translational-activating sequence, and
(2) culturing said Streptomyces cell under conditions suitable for growth and gene expression.

The invention further comprises the transformants, vectors and the novel transcriptional- and translational-activating sequence required to employ the aforementioned method.

The present invention is exemplified by constructing vectors that express hygromycin B phosphotransferase in Streptomyces. This construction of an expression vector was done by ligating (1) the hygromycin B phosphotransferase-encoding ~1.3 kb BamHI-BglII restriction fragment of plasmid pOW20; (2) the ~6.6 kb EcoRI-BamHI restriction fragment of plasmid pFJ265; and (3) the transcriptional- and translational-activating sequence-containing linker:

```
5' AATTCTATTTGACAAAAATGGGCTCGTGTTGTATA
   |||||||||||||||||||||||||||||||||||
3'     GATAAACTGTTTTTACCCGAGCACAACATAT

ATAAATGTAAGCTTGTGAGGTGGATGCCATG          3'
   |||||||||||||||||||||||||||||||
   TATTTACATTCGAACACTCCACCTACGGTACCTAG 5'
``` wherein
A is deoxyadenyl,
G is deoxyguanyl,
C is deoxycytosyl and
T is thymidyl.

The resultant plasmid, designated as pFJ350, is selectable, autonomously replicating and capable of directing high level expression of hygromycin B phosphotransferase in Streptomyces host cells. A restriction site and function map of plasmid pFJ350 is presented in FIG. 1 of the accompanying drawings.

The starting materials used in the construction of plasmid pFJ350 are readily available. The DNA fragments used in the construction of the linker were synthesized either by using a Systec 1450A DNA Synthesizer (Systec Inc., 3816 Chandler Drive, Minneapolis, Minn.) or an ABS 380A DNA Synthesizer (Applied Biosystems, Inc., 850 Lincoln Centre Drive, Foster City, Calif. 94404). Many DNA synthesizing instruments are known in the art and can be used to make the fragments. In addition, the fragments can also be conventionally prepared in substantial accordance with the procedures of Itakura et al., 1977, Science, 198:1056 and Crea et al., 1978, Proc. Nat. Acad. Sci. USA, 75:5765. Plasmid pOW20 is obtained from *E. coli* K12 JA221/pOW20, a strain deposited at the Northern Regional Research Laboratory (NRRL), Peoria, Ill. 61604. *Escherichia coli* K12 JA221/pOW20 serves as a preferred source and stock reservoir of plasmid pOW20 under the accession number NRRL 15838. Plasmid pFJ265 is a plasmid pNM100 (NRRL 15156) derivative well-known in the art; the construction of plasmid pNM100 is described in both Jones et al., 1984, Plasmid, 11:92 and U.S. Pat. No. 4,468,462, incorporated by reference herein.

The transcriptional- and translational-activating sequence of the present invention was designed to facilitate the cloning and expression of genes in Streptomyces. Thus, the translational start signal present on the sequence can be located within a NcoI recognition sequence, allowing one to readily clone and express any gene which has its own translational start signal encoded within a similar sequence. Ligating the transcriptional- and translational-activating sequence of plasmid pFJ350 to such a gene at their respective NcoI sites ensures that the gene will be read and expressed in the correct reading phase.

Although genes that naturally contain a NcoI site at the translational start are preferred, genes lacking such sites can also be used. In the latter case, the gene can be cleaved by a restriction enzyme and then reconstructed synthetically so as to contain the desired NcoI sticky end. Alternatively, depending upon convenience and ease of construction, the modified gene may be entirely synthetic. In either case, the modified gene can be ligated to the NcoI sticky end of the present activating sequence, thus restoring the ATG methionine-encoding start triplet and allowing for the direct expression of a desired product.

The present transcriptional- and translational-activating sequence is easily modified to substitute the NdeI translational start signal-encoding recognition sequence for the aforementioned NcoI sequence. Preferred genes would then be those that naturally contain a NdeI recognition sequence at the translational start. Ligation of the thus modified transcriptional- and translational-activating sequence to such genes at their respective NdeI sites ensures that the genes will be read and expressed in the correct reading phase. Genes not containing an NdeI recognition sequence that encodes their translational start signal could be modified to have such a sequence.

In the construction of plasmid pFJ350, the 3' end of the transcriptional- and translational-activating sequence was constructed to have a four base pair, 5' overlap characteristic of BamHI restriction enzyme cleavage. The presence of this BamHI recognition sequence in the present activating sequence facilitates ligation of a functional polypeptide-encoding gene and allows for expression of a fused gene product. Although genes that naturally contain a BamHI site at or near the translational start point (but within the coding sequence) are preferred, genes lacking such sites can also be used. In the latter case, the gene can be cleaved by a restriction enzyme and then reconstructed synthetically so as to contain the desired BamHI overlap.

Other restriction enzyme recognition sequences can be attached to the present activating sequence to facilitate the construction of fusion polypeptide-encoding genes. Although the use of the BamHI recognition sequence was exemplified, it is not difficult to replace the aforementioned BamHI recognition sequence with that of BglII, SacI or almost any other restriction enzyme. These modifications would facilitate the ligation of the present transcriptional- and translational-activating sequence to genes that contain any restriction enzyme recognition sequence in their coding region near the translational start point.

In the construction of plasmid pFJ350, the 5' end of the activating sequence was constructed with a four base pair overlap characteristic of EcoRI restriction enzyme cleavage. The presence of this EcoRI overlap on the present activating sequence facilitated the construction of plasmid pFJ350 since the plasmid pFJ265 starting material had an EcoRI site available for cloning. Although other plasmids can be expected to have different restriction sites available for cloning, the present activating sequence can be readily modified to be compatible with these sites also.

Although the various modifications of the transcriptional- and translational-activating sequence described above facilitate the construction of assorted illustrative vectors, the present activating sequence can also be inserted into an expression vector as a bluntended molecule. The varied design features and modifications described demonstrate both that the present activating sequence is useful in a wide variety of expression vectors and that the present method for expressing a functional polypeptide in Streptomyces represents a significant technical advance.

The present method is particularly versatile and can be applied to the production in Streptomyces of any polypeptide which can be encoded by a gene in a recombinant DNA expression vector. A preferred recombinant DNA expression vector is a plasmid, although bacteriophage and other vectors can also be used and are apparent to those skilled in the art. In addition to the illustrative hygromycin resistance-conferring gene, other genes that can be used include genes that are naturally occurring, genes that are non-naturally occurring and genes that are in part naturally occurring and in part synthetic or non-naturally occurring. More particularly, the genes can code for human preproinsulin, human proinsulin, human insulin A-chain, human insulin B-chain, non-human insulin, tissue plasminogen activator, growth hormone releasing factor, human growth hormone releasing factor, human growth hormone, non-human growth hormone, bovine growth hormone, porcine growth hormone, interleukin I, interleukin II, IGF1, IGF2, human interferon, non-human interferon, viral antigen, urokinase, a polypeptide hormone, a polypeptide enzyme or virtually any other polypeptide with research or commercial value.

The present method for expressing a functional polypeptide in Streptomyces is not limited to a single species or strain of Streptomyces. To the contrary, the present invention is broadly applicable and can be applied to host cells of many Streptomyces taxa, particularly the restrictionless strains thereof. Restrictionless strains are readily selected and isolated from Streptomyces taxa by conventional procedures well-known in the art (Lomovskaya et al., 1980, Microbiological Reviews 44:206). Host cells of restrictionless strains lack restriction enzymes and therefore do not cut or degrade DNA upon transformation. For purposes of the present application, host cells containing restriction enzymes that do not cut any of the restriction sites of the vectors that are useful for illustrating the present invention are also considered restrictionless.

Preferred host cells of restrictionless strains of Streptomyces taxa that produce aminoglycoside antibiotics, and in which the present method can be applied and is especially useful, include restrictionless cells of, for example S. kanamyceticus (kanamycins), S. chrestomyceticus (aminosidine), S. griseoflavus (antibiotic MA 1267), S. microsporeus (antibiotic SF-767), S. ribosidificus (antibiotic SF733), S. flavopersicus (spectinomycin), S. spectabilis (actinospectacin), S. rimosus forma paromomycinus (paromomycins, catenulin), S. fradiae var. italicus (aminosidine), S. bluensis var. bluensis (bluensomycin), S. catenulae (catenulin), S. olivoreticuli var. cellulophilus (destomycin A), S. tenebrarius (tobramycin, apramycin), S. lavendulae (neomycin), S. albogriseolus (neomycins), S. albus var. metamycinus (metamycin), S. hygroscopicus var. sagamiensis (spectinomycin), S. bikiniensis (streptomycin), S. griseus (streptomycin), S. erythrochromogenes var. narutoensis (streptomycin), S. poolensis (streptomycin), S. galbus (steptomycin), S. rameus (streptomycin), S. olivaceus (streptomycin), S. mashuensis (streptomycin), S. hygroscopicus var. limoneus (validamycins), S. rimofaciens (destomycins), S. hygroscopicus forma glebosus (glebomycin), S. fradiae (hybrimycins, neomycins), S. eurocidicus (antibiotic A16316-C), S. aquacanus (N-methyl hygromycin B), S. crystallinus (hygromycin A), S. noboritoensis (hygromycin), S. hygroscopicus (hygromycins), S. atrofaciens (hygromycin), S. kasugaspinus (kasugamycins), S. kasugaensis (kasugamycins), S. netropsis (antibiotic LL-AM31), S. lividus (lividomycins), S. hofuensis (seldomycin complex) and S. canus (ribosyl paromamine).

Preferred host cells of restrictionless strains of Streptomyces taxa that produce macrolide antibiotics, and in which the present method can be applied and is especially useful, include restrictionless cells of, for example: S. caelestis (antibiotic M188), S. platensis (platenomycin), S. rochei var. volubilis (antibiotic T2636), S. venezuelae (methymycins), S. griseofuscus (bundlin), S. narbonensis (josamycin, narbomycin), S. fungicidicus (antibiotic NA-181), S. griseofaciens (antibiotic PA133A, B), S. roseocitreus (albocycline), S. bruneogriseus (albocycline), S. roseochromogenes (albocycline), S. cinerochromogenes (cineromycin B), S. albus (albomycetin), S. felleus (argomycin, picromycin), S. rochei (lankacidin, borrelidin), S. violaceoniger (lankacidin), S. griseus (borrelidin), S. maizeus (ingramycin), S. albus var. coilmyceticus (coleimycin), S. mycarofaciens (agetylleukomycin, espinomycin), S. hygroscopicus (turimycin, relomycin, maridomycin, tylosin, carbomycin), S. griseospiralis (relomycin), S. lavendulae (aldgamycin), S. rimosus (neutramycin), S. deltae (deltamycins), S. fungicidicus var. espinomyceticus (espinomycins), S. furdicidicus (mydecamycin), S. ambofaciens (spiramycin, foromacidin D), S. eurocidicus (methymycin), S. griseolus (griseomycin), S. flavochromogenes (amaromycin, shincomycins), S. fimbriatus (amaromycin), S. fasciculus (amaromycin), S. erythreus (erythromycins), S. antibioticus (oleandomycin), S. olivochromogenes (oleandomycin), S. spinichromogenes var. suragaoensis (kujimycins), S. kitasatoensis (leucomycin), S. narbonensis var. josamyceticus (leucomycin A3, josamycin), S. albogriseolus (mikonomycin), S. bikiniensis (chalcomycin), S. cirratus (cirramycin), S. djakjartensis (niddamycin), S. eurythermus (angolamycin), S. fradiae (tylosin, lactenocin, macrocin), S. goshikiensis (bandamycin), S. griseoflavus (acumycin), S. halstedii (carbomycin), S. tendae (carbomycin), S. macrosporeus (carbomycin), S. thermotolerans (carbomycin) and S. albireticuli (carbomycin).

Preferred host cells of restrictionless strains of Streptomyces taxa that produce β-lactam antibiotics, and in which the present method can be applied and is especially useful, include restrictionless cells of, for example: S. lipmanii (A16884, MM4550, MM13902), S. clavuligerus (A16886B, clavulanic acid), S. lactamdurans (cephamycin C), S. griseus (cephamycin A, B), S. hygroscopicus (deacetoxycephalosporin C), S. wadayamensis (WS-3442-D), S. chartreusis (SF 1623), S. heteromorphus and S. panayensis (C2081X); S. cinnamonensis, S. fimbriatus, S. halstedii, S. rochei and S. viridochromogenes (cephamycins A, B); S. cattleya (thienamycin); and S. olivaceus, S. flavovirens, S. flavus, S. fulvoviridis, S. argenteolus and S. sioyaensis (MM 4550 and MM 13902).

Preferred host cells of restrictionless strains of Streptomyces taxa that produce polyether antibiotics, and in which the present method can be applied and is especially useful, include restrictionless cells of, for example: S. albus (A204, A28695A and B, salinomycin), S. hygroscopicus (A218, emericid, DE3936), A120A, A286-95A and B, etheromycin, dianemycin), S. griseus (grisorixin), S. conglobatus (ionomycin), S. eurocidicus var. asterocidicus (laidlomycin), S. lasaliensis (lasalocid), S. ribosidificus (lonomycin), S. cacaoi var. asoensis (lysocellin), S. cinnamonensis (monensin), S. aureofaciens (narasin), S. gallinarius (RP 30504), S. longwoodensis (lysocellin), S. flaveolus (CP38936), S. mutabilis (S-11743a) and S. violaceoniger (nigericin).

Preferred host cells of restrictionless strains of Streptomyces taxa and related genera such as, for example, Nocardia that produce glycopeptide antibiotics, and in which the present method can be applied and is especially useful, include restrictionless cells of, for example: *Nocardia orientalis* and *S. haranomachiens* is (vancomycin); *Nocardia candidus* (A-35512, avoparcin); *S. eburosporeus* (LL-AM 374); *S. virginiae* (A41030); and *S. toycaensis* (A47934).

Preferred host cells of other Streptomyces restrictionless strains, in which the present method can be applied and is especially useful, include restrictionless cells of, for example: *S. coelicolor, S. granuloruber, S. roseosporus, S. lividans, S. espinosus S. azureus, S. griseofuscus, S. fradiae, S. ambofaciens* and *S. toyocaensis*.

While all the embodiments of the present invention are useful, some of the expression vectors and transformants are preferred for applying the present invention. Accordingly, a preferred vector is plasmid pFJ350 and a preferred transformant is *Streptomyces ambofaciens*/pFJ350.

Plasmid pFJ350 is especially useful as a cloning vector due to the presence of two antibiotic resistance-conferring genes on the plasmid. Insertional inactivation of one of the genes provides a convenient way of cloning and selecting for the presence of otherwise non-selectable DNA. As an example, a non-selectable DNA fragment can be inserted into the SalI site of the thiostrepton resistance-conferring gene on plasmid pFJ350, thereby inactivating the thiostrepton resistance-conferring gene. Transformants containing the thus modified plasmid pFJ350 are easily distinguished from unmodified plasmid pFJ350-containing transformants by their distinctive hygromycin-resistant, thiostreptonsensitive phenotype.

Not only is the hygromycin phosphotransferase gene product expressed by plasmid pFJ350 useful as a selectable marker, but the gene product is also useful as a molecular weight marker. The entire amino acid sequence of the hygromycin gene product is known and the molecular weight of the protein is 37,972 daltons. The hygromycin phosphotransferase enzyme may be purified in substantial accordance with the teachings of Haas and Downing, 1978, Methods in Enzymology, 48:611. The molecular weight of the hygromycin phosphotransferase protein is conveniently between the highest molecular weight of BIORAD's (32nd and Griffin Ave., Richmond, Calif. 94804-9989) Low Molecular Weight Protein Standards and the lowest molecular weight of BIORAD's High Molecular Weight Protein Standards. BIORAD's protein standards are quite well-known in the art, and the hygromycin resistance gene product of plasmid pFJ350 conveniently expands the size range of either the Low or High Molecular Weight Protein Standards.

*Streptomyces ambofaciens*/pFJ350 can be cultured in a number of ways using any of several different media. Carbohydrate sources which are preferred in a culture medium include, for example, molasses, glucose, dextrin and glycerol. Nitrogen sources include, for example, soy flour, amino acid mixtures and peptones. Nutrient inorganic salts are also incorporated and include the customary salts capable of yielding sodium, potassium, ammonium, calcium, phosphate, chloride, sulfate and like ions. As is necessary for the growth and development of other microorganisms, essential trace elements are also added. Such trace elements are commonly supplied as impurities incidental to the addition of other constituents of the medium. *Streptomyces ambofaciens*/pFJ350 is grown under aerobic culture conditions over a relatively wide pH range of 5 to 9 at temperatures ranging from 15° to 40° C. and is resistant to a hygromycin concentration of 200 μg/ml.

The method for expressing functional polypeptides of the present invention has broad utility and helps fill the need for expression vectors and methods for use in Streptomyces. Thus, the present method allows for the genetic expression in Streptomyces of products now bioproduced in *E. coli* or *Bacillus*. This is especially advantageous because large scale fermentation of Streptomyces is better known and understood than is fermentation of either *E. coli* or *Bacillus*. In fact, commercial fermentation of *E. coli* is still highly experimental and fraught with difficulty. The present invention circumvents this problem by providing the alternative of producing compounds now biosynthesized in *E. coli* such as, for example, human insulin, human proinsulin, glucagon, interferon, human growth hormone, bovine growth hormone and the like in Streptomyces. This can be done because the vectors useful in the present method are highly versatile and can accommodate DNA sequences which encode the aforementioned products. The present method thus allows for flexibility in the choice of hosts and provides a means for using Streptomyces in the bioproduction of polypeptides and other gene products. Therefore, the use of a synthetic transcriptional- and translational-activating DNA sequence for the genetic expression of functional polypeptides in Streptomyces allows for the full exploitation of recombinant DNA technology in that industrially important class of microorganisms.

The following examples further illustrate and detail the invention disclosed herein. Both an explanation of and the actual procedures for constructing the invention are described where appropriate.

EXAMPLE 1

Isolation of Plasmid pNM100

A. Culture of *Streptomyces virginiae*/pNM100

Figure 1:
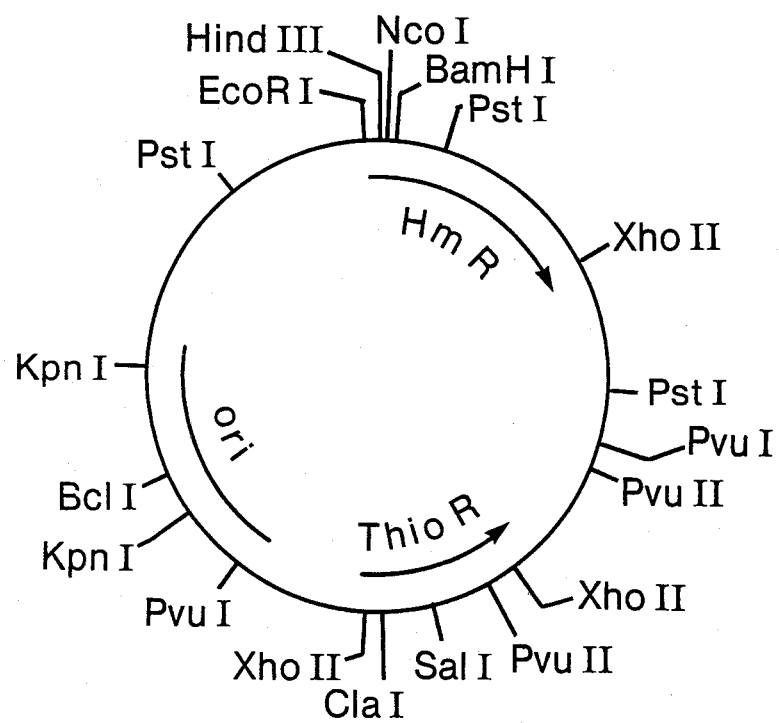
FIG. 1—the restriction site and function map of plasmid pFJ350.

A vegetative inoculum of *Streptomyces virginiae*/pNM100 (NRRL 15156) was con;entionally prepared by growing the strain under submerged aerobic conditions in 50 ml of sterilized trypticase soy broth* at 35 g/l in deionized water.

The trypticase soy broth inoculum was incubated for 48 hours at a temperature of 30° C. About 10 ml of the incubated inoculum were first transferred to 500 ml of sterilized broth and then incubated for about 20 hours at 30° C. The pH was not adjusted. After incubation, the *Streptomyces virginiae*/pNM100 cells were ready for harvest and subsequent isolation of plasmid DNA.

*Trypticase soy broth is obtained from Difco Laboratories, Detroit, Mich.

B. Plasmid Isolation

About 10 g (wet wt.) of *Streptomyces virginiae*/pNM100 cells were harvested by centrifugation (10 minutes, 5° C., 10,000 rpm) in a GSA rotor (DuPont, Biomedical Division, Newport, Conn. 06470). The cells were homogenized using a tissue grinder and then suspended in 10 ml of a solution that was: 25 mM Tris-HCl, pH 8; 10 mM EDTA; and 50 mM glucose. After the addition of 400 mg of lysozyme and 2 mg heat-treated RNAse A, the suspension was incubated at 35°–37° C.

for about 30 minutes. Following this incubation, 20 ml of a solution of 0.2 N NaOH and 1% SDS were added and the suspension mixed and then incubated on ice for 5-10 minutes. Then 15 ml of 3 M NaOAc, pH 4.8, were added to the solution, which was then mixed and incubated on ice for 1 hour. The mixture was then centrifuged in an SS34 rotor (DuPont) at 15,000 rpm for 20 minutes. The pellet was discarded, and the DNA in the supernatant was precipitated with ethanol and then resuspended in TE buffer (10 mM Tris-HCl, pH 8 and 1 mM EDTA). After phenol-CHCl$_3$ and CHCl$_3$ extractions, the DNA was pelleted by making the solution 0.3 M in NaOAc and adding 2 volumes of ethanol, chilling to −70° C. and centrifuging in an SS34 rotor at 15,000 rpm for 10 minutes. The pellet was resuspended in 1 ml 1/10 TE buffer and added to 4.14 g cesium chloride, 1.84 ml of STE (10 mM Tris-HCl, pH 8; 10 mM NaCl; and 1 mM EDTA, pH 8), 0.5 ml EDTA (0.25 M, pH 8) and 0.8 ml ethidium bromide (5 mg/ml), resulting in a 5.1 ml gradient with 1.6 g/ml cesium chloride and 800 μg/ml ethidium bromide. Centrifugation (5 hours, 20° C., 60,000 rpm) in an ultracentrifuge with a vertical rotor, such as Beckman VTi65 (Beckman Instruments Inc., Spinco Division, 1117 California Avenue, Palo Alto, Calif. 94304), followed by deceleration for ∼1.3 hours without breaking, resulted in well-defined bands. The lower band constitutes the desired plasmid pNM100. Following conventional procedures, the plasmid band was removed, washed twice with isoamyl alcohol, dialyzed against TE buffer at pH 8.0 and precipitated with ethanol. The isolated plasmid pNM100 DNA was dissolved in 0.4 ml of TE buffer at pH 8.0 and was then frozen at −20° C. for storage.

EXAMPLE 2

Construction of Plasmid pNM103

A. Isolation of the ∼4.0 kb BamHI Replicon-Containing Restriction Fragment of Plasmid pNM100

About 50 μg of plasmid pNM100 DNA (NRRL 15156), 10 μl 10X BamHI buffer (1.5 MNaCl; 60 mM Tris-HCl, pH 7.9; and 60 mMMgCl$_2$), 10 μl BSA (1 mg/ml), 24 μl H$_2$O and 5 μBamHI (∼25 units) restriction enzyme were incubated at 37° C. for 2 hours. Then, after adding an equal volume of 4 M ammonium acetate and 2.5 volumes of 95% ethanol, the mixture was cooled to −20° C. and the resulting DNA precipitate collected by centrifugation. The DNA was then suspended in about 50 μl of TE buffer and the desired ∼4.0 kb fragment isolated conventionally by agarose gel electrophoresis in substantial accordance with the teaching of Davis et al., 1980, A Manual for Genetic Engineering, Advanced Bacterial Genetics, Cold Spring Harbor Laboratories, Cold Spring Harbor, N.Y. Following isolation, the fragment was suspended in about 10 μl of TE buffer for subsequent ligation.

B. Isolation of the ∼0.8 kb BclI Thiostrepton Resistance-Conferring Restriction Fragment of Plasmid pLR2

About 50 μg of plasmid pLR2 DNA (subject matter of and claimed in U.S. Pat. No. 4,416,994, of which the construction of plasmid pLR2 is incorporated by reference herein), 10 μl BclI reaction mix*, 10 μl BSA (1 mg/ml), 24 μl H$_2$O and 5 μl BclI (∼25 units) restriction enzyme were incubated at 50° C. for 2 hours. Plasmid pLR2 must be obtained from a dam$^-$ organism in order to be digested with BclI; E. coli GM48 (NRRL B- 15725) is recommended. Following the reaction, the BclI-digested DNA was precipitated and the desired 0.8 kb fragment isolated in substantial accordance with the teaching of Example 2A. The fragment was suspended in 10 μl of TE buffer and stored at −20° C.

*BclI reaction mix is:
750 mM KCl
60 mM Tris-HCl, pH 7.4
10 mM dithiothreitol
100 mM MgCl$_2$

C. Ligation of the ∼4.0 kb BamHI Replicon-Containing Fragment to the ∼0.8 kb BclI Thiostrepton Resistance-Conferring Fragment About 5 μl of the DNA prepared in Example 2A were added to 5 μl of the DNA prepared in Example 2B, 3 μl BSA (∼1 mg/ml), 1 μl T4 DNA ligase (∼100 Units), 3 μl 10X ligase mix* and 13 μl of H$_2$O, gently mixed and reacted at 16° C. for 4 hours. The reaction was terminated by the addition of 30 μl 4 M ammonium acetate and 120 μl of 95% ethanol. After mixing and chilling to −70° C., the DNA was pelleted by centrifugation and the supernatant discarded. The DNA pellet was resuspended in 10 μl of TE and constituted the desired plasmid pNM103.

* Ligation mix was prepared with the following composition:
500 mM Tris-HCl, pH 7.8
200 mM dithiothreitol
100 mM MgCl$_2$
10 mM ATP

EXAMPLE 3

Construction of Streptomyces ambofaciens/pNM103

Using about 1 μg of the DNA from Example 2C and 1×10$^8$ protoplasts of Streptomyces ambofaciens, a strain deposited and made part of the permanent stock culture collection of the Northern Regional Research Laboratory, Peoria, Ill., from which it is available to the public under the accession number NRRL 2420, the desired constructions were made in substantial accordance with the teaching of Example 2 in International Publication (of International patent application No. PCT/GB79/00095) No. W079/01169 and also Example 9 of U.S. Pat. No. 4,416,994. The desired transformants were selected for thiostrepton resistance by overlaying the regenerating protoplasts with R2 medium (Hopwood and Wright, 1978, Molecular and General Genetics 162:30) top agar containing sufficient thiostrepton to bring the final plate concentration to 50 μg/ml. The resultant Streptomyces ambofaciens/pNM103 thiostrepton-resistant colonies were isolated according to known procedures, cultured and then conventionally identified by restriction enzyme and agarose gel electrophoretic analysis of the constitutive plasmids (Davis et al., 1980). The transformant cultures were then used for subsequent production and isolation of their respective plasmids by substantial accordance with the teaching of Example 1.

EXAMPLE 4

Construction of Plasmid pFJ265

A. Isolation of the ∼4.2 kb Partial PstI Restriction Fragment of Plasmid pLR4

About 50 μl (50 μg) of plasmid pLR4 (subject matter of and claimed in U.S. Pat. No. 4,416,994, of which construction of pLR4 is incorporated by reference herein), 10 μl PstI reaction mix*, 10 μl BSA (1 mg/ml), 1 μl PstI restriction enzyme and 29 μl H$_2$O were mixed and incubated 15 minutes at 37° C. The reaction was terminated by the addition of 50 μl of phenol (pH 8) and subsequent extraction. The desired ~4.2 kb PstI fragment was then isolated in substantial accordance with the teaching of Example 2A. The fragment is suspended in 20 μl of TE buffer and stored at −20° C.

*PstI reaction mix is:
1 M NaCl
100 mM Tris-HCl, pH 7.5
100 mM MgCl₂

B. PstI Digestion of Plasmid pNM103

About 5 μg (5 μl) of plasmid pNM103 (see Example 2), 5 μl PstI reaction mix, 5 μl BSA (1 mg/ml), 1 μl PstI restriction enzyme and 34 μl of H₂O were mixed and incubated at 37° C. for 2 hours. The reaction was terminated by phenol (pH 8) and CHCl₃ extractions. The DNA was then precipitated and resuspended in 10 μl of TE buffer.

C. Ligation of the ~4.2 kb Partial PstI Restriction Fragment of Plasmid pLR4 to PstI-Digested Plasmid pNM103

About 5 μl of the DNA prepared in Example 4A were ligated to 5 μl of the DNA prepared in Example 4B in substantial accordance with the teaching of Example 2C. The ligated DNA constituted the desired plasmid pFJ265.

EXAMPLE 5

Construction of *Streptomyces ambofaciens*/pFJ265

The desired construction was carried out in substantial accordance with the teaching of Example 3 except that plasmid pFJ265, rather than plasmid pNM103, was used for the transformation. Surviving colonies were selected and tested both for the expected phenotype (Thio^R, Neo^R), and for the presence of expected restriction endonuclease recognition sites in the harbored plasmid DNA. The transformants so tested constituted the desired *Streptomyces ambofaciens*/pFJ265. Plasmid pFJ265 DNA is obtained from these transformants by substantial accordance with the teaching of Example 1.

EXAMPLE 6

Construction of a Synthetic Streptomyces Transcriptional and Translational Activating DNA Sequence

A. Synthesis of Single-Stranded DNA Fragments

The single-stranded DNA fragments were synthesized either by using a Systec 1450A DNA Synthesizer or an ABS 380A DNA Synthesizer. Many other DNA Synthesizers are known in the art and can be used to make the fragments. In addition, th=fragments can be conventionally synthesized in substantial accordance with the aforementioned teachings of Itakura et al., 1977, and Crea et al., 1978. The fragments synthesized were:

(1) 5' GGAATTCTATTT-GACAAAAATGGGCTCGTGTTGTAT AA-TAAATGTA 3', a 46-mer,
(2) 5' CACAAGCTTACATTTATTA, a 19-mer,
(3) 5' AGGTGGATGCCATG, a 14-mer, and,
(4) 5' GATCCATGGCATCCACCT, an 18-mer.

B. Synthesis of Double-Stranded DNA Fragment I

Six hundred picomoles of 5'-phosphorylated (with tracer amounts of γ-³²P-ATP added during the phosphorylation reaction) fragments 1 and 2 of Example 6A were annealed in 10 μl 10X Klenow buffer* and then treated with the Klenow fragment of DNA Polymerase I (~10 units) to form a completely double-stranded, blunt-ended DNA molecule. After the Klenow reaction at 37° C. for 30 minutes, the reaction mix was passed through a Sephadex G-50 column. The radioactive fractions were then pooled and lyophilized to dryness. The residue was dissolved in 30 μl 5X EcoRI buffer and then treated with EcoRI restriction enzyme to generate a 5', four base bair overlap characteristic of enzyme EcoRI cleavage. The resulting DNA molecule had the following structure:

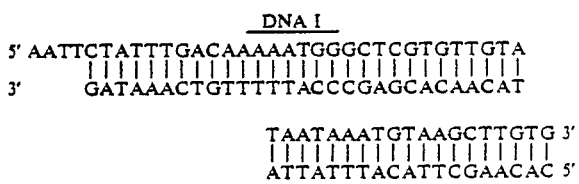

This DNA molecule was isolated from the reaction by electrophoresis on a 20% polyacrylamide gel.

*10X Klenow buffer is:
600 mM NaCl
66 mM MgCl₂
100 mM Tris-HCl, pH 7.6
500 μM in each of the dNTP
60 mM dithiothreitol

**5X EcoRI buffer is:
500 mM Tris-HCl, pH 7.5
25 mM MgCl₂
0.5 mg/ml BSA
250 mM NaCl

C. Synthesis of Double-Stranded DNA Fragment II

Five hundred and eight picomoles of 5'-phosphorylated (with tracer amounts of γ-³²P-ATP added during the phosphorylation reaction) fragments 3 and 4 of Example 6A were annealed to form DNA Fragment II. Fragment II has an overlap characteristic of BamHI on one end of the molecule and is blunt-ended on the other end. DNA Fragment II has the structure:

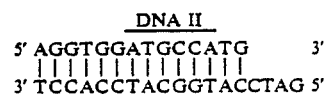

EXAMPLE 7

Culture of *E. coli* JA221/pOW20 and Isolation of Plasmid pOW20

A. Culture of *E. coli* JA221/pOW20

A 2 ml culture of *E. coli* JA221/pOW20 (NRRL B-15838) was grown in the presence of 50 μg/ml ampicillin in TY media (1% tryptone, 0.5% NaCl and 0.5% yeast extract, pH 7.4) until the cells reached stationary phase.

The 2 ml culture was then used to inoculate a flask containing 1 liter of TY media containing 50 μg/ml ampicillin, and growth was continued until the optical density at 550 nanometers was between 0.50 and 0.75. When the O.D. 550 reached the 0.50–0.75 absorbance units range, 1 g of uridine was added, and, 15 minutes later, 170 mg of chloramphenicol was added. The incubation and culturing was then continued for 16 hours.

B. Isolation of Plasmid pOW20

The culture was centrifuged and the cell pellet resuspended in 10 ml of a solution that was 25% w/v sucrose; 50 mM Tris-HCl, pH 8; and 1 mM EDTA. Then 2 ml of 0.5 M EDTA and 2 ml of a 5 mg/ml lysozyme solution in 0.25 M Tris-HCl, pH 8 were added to the resuspended cell pellet and the resultant mixture incubated at room temperature for 15 minutes. After the 15 minute incubation, 14 ml of a solution that was 50 mM Tris-HCl, pH 8; 6 mM EDTA; and 0.1% Triton X-100 were added to the lysozyme-treated cells and mixed by inversion.

The lysed cell mix was then centrifuged until the cell debris formed a loose pellet. The cell debris pellet was discarded and the supernatant extracted with buffered (pH 8) phenol. After phenol extraction, the aqueous phase was made 0.25 M in NaCl and two volumes of ethanol were added. After chilling the resultant mixture to −70° C., the nucleic acid was pelleted by centrifugation.

Further centrifugation (45,000 rpm, 16 hours, 20° C.) using cesium chloride gradients with ethidium bromide, was carried out to purify the plasmid DNA. Following centrifugation, the desired plasmid pOW20 DNA was collected and the ethidium bromide and cesium chloride removed by conventional procedures. The approximately 1 mg of plasmid pOW20 DNA obtained by this procedure was dissolved in 1 ml of TE buffer (10 mM Tris-HCl, pH 8 and 1 mM EDTA) and stored at −20° C.

EXAMPLE 8

Construction of Plasmid pFJ350

A. Isolation of the ~1.3 kb BamHI-BglII Restriction Fragment of pOW20 Containing the Truncated Hygromycin Resistance Gene About 50 μg (50 μl) of plasmid pOW20 prepared in Example 7 were mixed with 10 μl of 10X BamHI-BglII reaction mix*, 5 μl (~50 Units) BamHI restriction enzyme, 5 μl (~50 Units) BglII restriction enzyme, 20 μl H2O and 10 μl BSA (1 mg/ml) and allowed to react at 37° C. for 2 hours. After reacting, the digest was extracted with buffered phenol and the desired ~1.3 kb fragment isolated by conventional electrophoretic gel means. The ~10 μg of fragment obtained were resuspended in 10 μl of TE buffer and stored at −20° C.

*10X BamHi-BglII reaction mix is:
1.5 M NaCl
80 mM Tris-HCl, pH 7.7
80 mM MgCl2
10 mM 2-mercaptoethanol

B. Isolation of the ~6.6 kb EcoRI-BamHI Restriction Fragment of Plasmid pFJ265 Containing a Streptomyces Replicon and a Thiostrepton Resistance-Conferring Gene About 50 μg (50 μl) of plasmid pFJ265 (Examples 4 and 5) were mixed with 10 μl BamHI reaction mix, 5 μl (~50 Units) BamHI restriction enzyme and 35 μl H2O and reacted at 37° C. for 2 hours. The reaction mix was then made 0.25 M in NaCl and two volumes of ethanol were added, mixed and the mixture placed in a dry ice-ethanol bath for 10 minutes. The mixture was then centrifuged to pellet the DNA; the supernatant was discarded. The BamHI-cut plasmid pFJ265 DNA was then resuspended in a mixture of 10 μl EcoRI reaction mix, 5 μl (~50 Units) EcoRI restriction enzyme and 85 μl of H2O. The reaction was placed at 37° C. for 2 hours. After reacting, the reaction was extracted once with buffered phenol and the desired ~6.6 kb EcoRI-BamHI fragment isolated by conventional electrophoretic gel means. The ~10 μg of fragment obtained were suspended in 20 μl of TE buffer and stored at −20° C.

C. Ligation of DNA I, DNA II, the ~1.3 kb BamHI-BglII Restriction Fragment of Plasmid pOW20, and the ~6.6 kb EcoRI-BamHI Restriction Fragment of Plasmid pFJ265 to Form Plasmid pFJ350

About 2 μg of the ~1.3 kb BamHI-BglII restriction fragment obtained in Example 8A are mixed with 2 μg of the ~6.6 kb EcoRI-BamHI restriction fragment obtained in Example 8B, 5 picomoles of DNA I prepared in Example 6B and 5 picomoles of DNA II prepared in Example 6C and ligated in substantial accordance with the teaching of Example 2C, except that the ligation is done at 4° C. for 16 hours. The ligated DNA constitutes the desired plasmid pFJ350.

EXAMPLE 9

Construction of Streptomyces ambofaciens/pFJ350

Using about 1 μg of the plasmid pFJ350 DNA obtained in Example 8C and following in substantial accordance the teaching of Example 3, the desired Streptomyces ambofaciens/pFJ350 transformants were constructed. Although Example 3 teaches thiostrepton selection, the preferred selection method uses the antibiotic hygromycin overlayed in R2* top agar at a concentration that provides 200 μg/ml of hygromycin after diffusion throughout the transformation plate. The hygromycin overlay is done about 16 hours after transformation to allow protoplast regeneration prior to antibiotic addition. Hygromycin selection is preferred because it illustrates the functionality and utility of the transcriptional- and translational-activating sequence of the present invention.

*R2 top agar is, per liter: 103 g sucrose; 10.12 g MgCl2.6H2O; 100 ml CaCl2 (2.22 g/100 ml); 100 ml TES buffer (5.73 g/100 ml, pH=7.2); 7 g agar; and made up to 1 liter with H2O.

EXAMPLE 10

Assay of Hygromycin Phosphotransferase Activity

Cells may be assayed for hygromycin phosphotransferase activity at any point in their life cycle. Streptomyces ambofaciens (NRRL 2420) can be used as a negative control.

A. Preparation of Protein Extract

Approximately 10 g of Streptomyces ambofaciens/pFJ350 were collected by centrifugation and washed once with 10 ml of 10 mM Tris-HCl, pH 8. After washing, the cells were resuspended in 5 ml of a solution that was 10 mM Tris-HCl, pH 8; 0.5 mM MgCl2; 0.1 mM EDTA; and 1.0 mM DTT. The cells were then sonicated with a Branson Sonifier Cell Disrupter (Branson Sonic Power Co., Eagle Rd., Conn. 06810) using the microtip at setting 7. The sonication was done in a set of five, fifteen-second bursts with the cells kept on ice for one minute between each burst.

After sonication, the mixture was centrifuged at 16,000 rpm in an SS34 (Sorvall) rotor at 4° C. for 30 minutes. The debris pellet was discarded and the supernatant made 4 μg/ml in DNAseI. The supernatant was then centrifuged at 45,000 rpm in a Ti75 rotor (Beckman) at 4° C. for 2 hours. Aliquots of 0.5 ml were then prepared and stored at −70° C. Protein concentrations of the aliquots were determined using the BIORAD Protein Assay.

B. Assay

The assay mix was prepared by first mixing: 4 μl 100 mM hygromycin B in H₂O; 10 μl 10X TMN buffer (10×TMN is 130 mM Tris-HCl, pH 8; 84 mM MgCl₂; and 800 mM NH₄Cl); 2 μl 100 mM DTT; and 20 μl 10 mM ATP containing ~5 μCi γ-³²P-ATP The reaction was initiated by the addition of 30 μg protein extract with enough H20 added to bring the reaction volume to 100 μl. The reaction was incubated at 37° C. for 15 minutes, and then 75 μl were removed and spotted onto three 2.4 cm Whatman P-81 phosphocellulose filters (Whatman Chemical Separation, Inc., 9 Bridewell Place, Clifton, N.J. 07014). The filters were then placed in an 80° C. water bath for 5 minutes to stop the reaction, washed with running water and dried. The radioactivity of the filters was determined by putting the filters into 5 ml of PCS scintillation fluid (Amersham/Searle, 2636 South Clearbrook Drive, Arlington Heights, Ill. 60005) and measuring the radioactivity for one minute in a scintillation counter set for ³²P measurement. Hygromycin phosphotransferase activity is evidenced by highly radioactive filters.

We claim:

1. A method for expressing a functional polypeptide in *Streptomyces ambofaciens* which comprises:
   (1) transforming a restrictionless *Streptomyces ambofaciens* host cell with a selectable recombinant DNA expression vector which autonomously replicates in or is integrated into the genome of said host cell, said vector comprising:
      (a) the transcriptional- and translational-activating sequence

wherein A is deoxyadenyl, G is deoxyguanyl, C is deoxycytosyl, and T is thymidyl; and
      (b) a DNA sequence that codes for a functional polypeptide positioned for expression and in the translational reading frame of said transcriptional- and translational- activating sequence, and
   (2) culturing said Streptomyces ambofaciens cell under conditions suitable for growth and gene expression.

2. The method of claim 1 wherein the transcriptional- and translational-activating sequence further comprises the sequence

wherein
A is deoxyadenyl,
G is deoxyguanyl,
C is deoxycytosyl,
T is thymidyl
and
R is the transcriptional- and translational-activating sequence as depicted in claim 1.

3. The method of claim 1 wherein the expression vector is a plasmid.

4. The method of claim 3 wherein the DNA sequence that codes for a functional polypeptide is selected from the group consisting of DNA sequences that code for human preproinsulin, human proinsulin, human insulin A-chain, human insulin B-chain, non-human insulin, human growth hormone releasing factor, human growth hormone, growth hormone releasing factor, non-human growth hormone, bovine growth hormone, porcine growth hormone, human interferon, non-human interferon, viral antigen, tissue plasminogen activator, interleukin I, interleukin II, and urokinase.

5. The method of claim 3 in which the DNA sequence encodes human proinsulin.

6. The method of claim 3 in which the DNA sequence encodes human insulin B-chain.

7. The method of claim 3 in which the DNA sequence encodes human growth hormone.

8. The method of claim 3 in which the DNA sequence encodes bovine growth hormone.

9. The method of claim 3 in which the DNA sequence encodes porcine growth hormone.

10. The method of claim 3 in which the DNA sequence encodes growth hormone releasing factor.

11. The method of claim 2 in which the recombinant DNA expression vector is plasmid pFJ350.

12. The method of claim 2 wherein the DNA sequence that codes for a functional polypeptide codes for a polypeptide enzyme.

13. The method of claim 2 wherein the DNA sequence that codes for a functional polypeptide codes for a polypeptide hormone.

14. A *streptomyces ambofaciens* host cell transformed with a recombinant DNA vector comprising:
   (a) the transcriptional- and translational- activating sequence

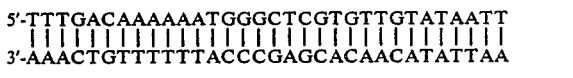

wherein A is deoxyadenyl, G is deoxyguanyl, C is deoxycytosyl, and T is thymidyl; and
   (b) a DNA sequence that codes for a functional polypeptide positioned for expression and in the translational reading frame of said transcriptional- and translational- activating sequence.

15. The *Streptomyces ambofaciens* host cell of claim 14, wherein said recombinant DNA vector is a plasmid.

16. The *Streptomyces ambofaciens* host cell of claim 15, wherein said recombinant DNA vector is plasmid pFJ350.

17. A constructed DNA compound that comprises the transcriptional and translational-activating sequence:

wherein A is deoxyadenyl, G is deoxyguanyl, C is deoxycytosyl, and T is thymidyl.

18. The DNA compound of claim 17 that is:

```
5'-GAATTCTATTTGACAAAAATGGGCTCGTGTTGT
   ||||||||||||||||||||||||||||||||||
3'-CTTAAGATAAACTGTTTTTACCCGAGCACAACA

ATAATAAATGTAAGCTTGTGAGGTGGATGCCA
   ||||||||||||||||||||||||||||||||
   TATTATTTACATTCGAACACTCCACCTACGGT

TGGATCC-3'
                         |||||||
                         ACCTAGG-5'
``` wherein A is deoxyadenyl, G is deoxyguanyl, C is deoxycytosyl, and T is thymidyl.

19. A recombinant DNA expression vector that comprises the transcriptional and translational-activating sequence of claim 17.

20. The recombinant DNA expression vector of claim 19 that is plasmid.

21. The recombinant DNA expression vector of claim 20 that is plasmid pFJ350.

22. The recombinant DNA expression vector of claim 19, wherein said activating sequence is positioned for expression of a polypeptide hormone.

23. The recombinant DNA expression vector of claim 19, wherein said activating sequence is positioned for expression of a polypeptide enzyme.

24. The recombinant DNA expression vector of claim 19, wherein said activating sequence is positioned for expression of a polypeptide selected from the group consisting of human preproinsulin, human proinsulin, human insulin A-chain, human insulin B-chain, non-human insulin, human growth hormone releasing factor, human growth hormone, growth hormone releasing factor, non-human growth hormone, bovine growth hormone, porcine growth hormone, human interferon, non-human interferon, viral antigen, tissue plasminogen activator, interleukin I, interleukin II, and urokinase.

25. The recombinant DNA expression vector of claim 19, wherein said activating sequence is positioned for expression of human proinsulin.

26. The recombinant DNA expression vector of claim 19, wherein said activating sequence is positioned for expression of human insulin B-chain.

27. The recombinant DNA expression vector of claim 19, wherein said activating sequence is positioned for expression of human growth hormone.

28. The recombinant DNA expression vector of claim 19, wherein said activating sequence is positioned for expression of bovine growth hormone.

* * * * *